(12) United States Patent
Hentrich et al.

(10) Patent No.: US 8,545,377 B2
(45) Date of Patent: Oct. 1, 2013

(54) MAGAZINE FOR CHAIN COMPONENTS FOR A CHAIN WITH RADIATION SOURCES AND A SYSTEM CONSISTING OF A CHAIN COMPONENT AND A MAGAZINE FOR CHAIN COMPONENTS FOR A CHAIN WITH RADIATION SOURCES

(75) Inventors: Axel Hentrich, Berlin (DE); Christoph Lederer, Berlin (DE)

(73) Assignee: Eckert & Ziegler Bebig GmbH, Berlin (DE)

( * ) Notice: Subject to any disclaimer, the term of this patent is extended or adjusted under 35 U.S.C. 154(b) by 194 days.

(21) Appl. No.: 13/025,780

(22) Filed: Feb. 11, 2011

(65) Prior Publication Data

US 2011/0201868 A1 Aug. 18, 2011

(30) Foreign Application Priority Data

Feb. 12, 2010 (EP) .................................... 10153450

(51) Int. Cl.
*A61M 36/00* (2006.01)
(52) U.S. Cl.
USPC ......... 600/7; 600/1; 600/3; 600/8; 250/493.1; 252/625; 424/1.11; 604/16; 604/17; 604/57; 604/59; 604/60; 604/61; 604/62; 604/63; 604/64; 221/4; 221/7; 221/8; 206/538
(58) Field of Classification Search
USPC ........... 600/1, 3, 7, 8; 604/16, 17, 57, 59–64; 221/4, 7, 8; 206/538; 250/493.1; 252/625; 424/1.11
See application file for complete search history.

(56) References Cited

U.S. PATENT DOCUMENTS

| | | | |
|---|---|---|---|
| 6,213,932 B1 * | 4/2001 | Schmidt ............................ 600/7 |
| 6,358,195 B1 | 3/2002 | Green et al. |
| 6,454,696 B1 | 9/2002 | Kindlein et al. |
| 6,572,527 B2 | 6/2003 | Steele, Sr. et al. |
| 6,616,593 B1 | 9/2003 | Elliott et al. |
| 6,648,711 B1 | 11/2003 | Jang et al. |
| 6,837,844 B1 | 1/2005 | Ellard et al. |
| 2002/0032360 A1 | 3/2002 | Fontayne |
| 2002/0193656 A1 | 12/2002 | Ravins |
| 2004/0077919 A1 | 4/2004 | Drobnik |

(Continued)

FOREIGN PATENT DOCUMENTS

WO    WO 2009/005528    1/2009

OTHER PUBLICATIONS

European Search Report issued for European Patent Application No. 10153450.1 mailed on Jul. 26, 2010.

*Primary Examiner* — Christine Matthews
*Assistant Examiner* — Sunita Reddy
(74) *Attorney, Agent, or Firm* — Pearl Cohen Zedek Latzer, LLP

(57) ABSTRACT

A magazine for chain components of a chain with radiation sources comprises a housing as well as a first means for receiving chain components that is mounted in a pivotal manner in the housing and has recesses for receiving the chain components, a tension spring for driving the means for receiving the chain components, a sprocket being coupled in a pivotal manner to the means for receiving the chain components and being mounted in a pivotal position in the housing, and an ejector for ejection of the radiation sources. Furthermore, the magazine comprises an ejection lever which is mounted in a pivotal manner in the housing, whereby, in a first position, the ejection lever engages the sprocket, and in a second position it blocks the ejector.

16 Claims, 19 Drawing Sheets

(56) References Cited

U.S. PATENT DOCUMENTS

| | | | |
|---|---|---|---|
| 2004/0162458 A1* | 8/2004 | Green et al. | 600/7 |
| 2005/0038312 A1* | 2/2005 | Green et al. | 600/7 |
| 2005/0267319 A1 | 12/2005 | White | |
| 2008/0161635 A1* | 7/2008 | Watson et al. | 600/7 |
| 2009/0105518 A1* | 4/2009 | Schreiber et al. | 600/7 |
| 2010/0106132 A1* | 4/2010 | Simonton | 604/506 |

* cited by examiner

MAGAZINE FOR CHAIN COMPONENTS FOR A CHAIN WITH RADIATION SOURCES AND A SYSTEM CONSISTING OF A CHAIN COMPONENT AND A MAGAZINE FOR CHAIN COMPONENTS FOR A CHAIN WITH RADIATION SOURCES

CROSS-REFERENCE TO RELATED APPLICATION

This application claims priority from European Patent Application No. 10153450.1, filed Feb. 12, 2010, which is hereby incorporated by reference in its entirety.

FIELD OF THE INVENTION

The invention relates to a magazine for chain components for a chain with radiation sources and a system of chain components and a magazine for chain components for a chain with radiation sources. The magazine is intended for the manufacture of chains made from radiation sources and spacers for treatment of prostate cancers in brachytherapy.

BACKGROUND OF THE INVENTION

It is known to implant in cancer patients, particularly prostate cancer patients, chains, or so-called seeds, made from radiation sources. To this end, single radiation sources are used as well as pre-configured seed chains constructed, for example, by alternating a radiation source and a non-active spacer. Implanting single radiation sources allows the single radiation sources to be positioned individually using suitable means. The inflammatory enlargement of the prostate after implantation, followed by swelling, can cause the radiation sources to migrate or shift its position. A radioactive chain prevents this shift in position because it connects the individual implants to each other.

New medical tests show that adherence to a radiation treatment individually tailored to the patient achieves the best results when treating tumors. To do this, the position of the individual radiation sources must be exactly adjusted to each patient.

WO 2009/005528 discloses a magazine and a device for joining freely configurable seed-spacer chains from a total of five different magazines with adjacent implants. The magazines lead the stacked chain components linearly downwards out of the magazines. However, this configuration is disadvantageous because the increasing number of chain components makes the magazines bulky and unhandy. Furthermore, since the magazines are made of transparent polymer, they are only radiation-proof in their packaging or after insertion into the loading device. For this reason, the magazine content is limited to about 20 radiation sources. As a result, when packaging more chains, the magazines must be changed. U.S. Pat. No. 6,454,696 B1 describes also linear magazines for the brachytherapy. In U.S. Pat. No. 6,648,711 B2 and U.S. Pat. No. 6,572,527 B2, the chain components are arranged one behind the other. However, this also has the disadvantage that the magazines cannot be arranged in a space-saving manner.

U.S. Pat. No. 6,616,593 B1 describes an automated round magazine for radiation sources in which different chain components, such as radiation sources and spacers, are placed in different chambers. Thereby the driving and the ejection of the chain components in the magazine are performed electrically. Thus the magazines depend on an external drive and there is no internal driving mechanism. This has the disadvantage that such a magazine cannot be sterilized completely.

In addition, the magazine must be replaced when, for example, the supply of spacer holders is spent but the supply of radiation sources is not. As a result, the operator can be exposed to irradiation while changing the magazine.

U.S. Pat. No. 6,454,696 B1 describes round magazines arranged successively, in which the radiation sources and the spacers are arranged concentrically with respect to the pivot point of the magazines. The magazines are again driven from outside. The implants are not ejected from the magazine but are placed in an opening inside the magazine and are dispatched by using an external wire. As a result, the spacer and the radiation source magazine are connected disadvantageously with each other, so that, constructively, the individual implants of the rear magazine have to be pushed through the magazine in front. However, the manual pushing through the different magazines leads often to jamming of the device which has again to be remedied manually. Manual pushing of chain components through different magazines is known also from U.S. Pat. No. 6,358,195 B1.

SUMMARY OF THE INVENTION

The purpose of the invention is to provide a magazine and a system for chain components of a chain with radiation sources which overcomes the disadvantages of the present state of the art.

Accordingly, it is an object of the invention to propose a magazine that can be fully sterilized. Another object is to place the chain components in the magazine in a space-saving manner. This allows the treating OP personnel to perform the seed implantation in an operator-friendly manner by following an individual irradiation plan. Operator-friendly means herewith respect both to the servicing of the magazine and the optimal radiation protection of the user.

Accordingly, a magazine for chain components of a chain with radiation sources is proposed which comprises a housing and a first means for receiving chain components that is mounted in a pivoting manner in the housing and has recesses or depressions for receiving the chain components, a tension spring for driving the means for receiving the chain components, a sprocket that is firmly coupled to the means for receiving the chain components and is mounted pivotally in the housing, and an ejector for ejection of the radiation sources. Furthermore, the magazine comprises an ejection lever which is mounted in a pivotal manner in the housing; in a first position, the ejection lever is built so that it engages the sprocket, and in a second position it blocks the ejection.

Advantageously, a magazine according to the invention does not require any electromechanical components for ejecting the chain components because it has its own drive in the form of a tension spring.

Preferably, the sprocket and the tension spring are formed integrally or in one piece. They can be manufactured in a simple and cost-effective manner by means of injection molding.

In a preferable embodiment, exactly a single ejector is provided which helps to minimize the radiation exposure.

The magazine is, preferably, configured specifically for one type of chain components. This means that it accepts either radiation sources or spacers, but, preferably, not both of them together.

Furthermore, the magazine comprises, preferably, a locking slider or sliding shutter for opening and closing the ejector, which is mounted slidably inside the housing. In addition, the locking slider permits minimization of radiation exposure. Particularly preferably, it is designed in a translationally slidable manner.

The means for receiving chain components is, preferably, designed in a circular form. The sprocket is, preferably, also designed in a circular form. In one embodiment, the recesses are arranged along the circumference of the means for receiving chain components. Their positioning along the circumference permits the reception of a large number of chain components.

Furthermore, a boundary can be provided in the housing around the means for receiving chain components. Preferably, the size of the distance of the boundary and the means for receiving the chain components can be designed in such a way that the chain components can be placed and guided between the means for receiving chain components and the boundary within the case. This means that the chain components can be guided along a circumference of the means for receiving chain components towards the ejection without falling out. This configuration permits a space-saving storage of the chain components and the preparation of magazines with up to 100 or more chain components.

Preferably, the tension spring is a constant force spring. This permits the ejection of the means for receiving chain components always with the same force.

The housing can have a circular inner bearing ring on which the constant force spring as well as the instrument for receiving the chain components and the above mounted sprocket are seated. Preferably, the constant force spring is mounted under the means for receiving chain components and the sprocket is mounted above the means for receiving chain components and they are connected to each other so that the constant force spring drives the means for receiving chain components.

The area of the means for receiving chain components, which is in contact with the inner bearing ring of the housing, can be designed to be visible from outside and provided with at least one mark for indication of the content. Preferably, this contact area is designed, accordingly, in the form of a ring.

Locking grooves can be provided at the housing for engaging locking elements for securing the magazine in a device for assembling of chain components.

Preferably, the case comprises a encoding opening, which acts together with the locking slider, so that when a respective encoding element is inserted in the encoding opening the locking slider deblocks the ejection. With the described encoding, it is impossible to interchange the radiation sources or the spacer magazine when an assembling device is used.

In a preferable embodiment, the ejection lever is biased by a first pressure spring and the locking slider is biased by a second pressure spring. The ejection lever can be activated from outside through a second opening in the housing.

Preferably, the ejector is mounted on the periphery of the magazine in such a way that the chain components can be ejected out of the magazine and away from the magazine. In an embodiment, the ejector is mounted on the bottom front side of the magazine. In this way, the chain components can be emitted downwards. It is neither necessary nor possible to push the chain components through the magazine from outside.

Preferably, an element is implemented for blocking a further rotation of the means for receiving chain components after an ejection of a chain component. This permits to eject always exactly one chain component. Preferably, the blocking function is taken over partially by the sprocket in connection with the ejection lever.

Preferably, the housing consists of radiation-absorbing material with stainless steel being particularly preferable. Thus, the radiation exposure can be further minimized.

Furthermore, a system of chain components for a chain with radiation sources and a magazine according to the invention is proposed, whereby an element for blocking a further rotation of the means for receiving chain components after ejection of a chain component is implemented by a joint action of the chain component following the ejected chain component and the ejection lever. In this way, also the chain components themselves can be used for blocking.

Preferably, in the said second position, the ejection lever blocks the ejector, and the chain component, which is next to the ejector, presses against the ejection lever, so that the rotation of the means for receiving chain components is blocked. Accordingly, a method for blocking the driving is further proposed.

BRIEF DESCRIPTION OF THE DRAWINGS

Exemplary embodiments of the invention are explained in the drawings and following descriptions.

DETAILED DESCRIPTION OF THE INVENTION

The present invention describes a magazine and a system for chain components of a chain that contains radiation sources. The magazine and the system are used in the manufacture of chains made from radiation sources and spacers for treatment of prostate cancer in brachytherapy. It can also be used for other applications, e.g. manufacturing chains with radiation sources to treat breast cancers.

Figure 1:
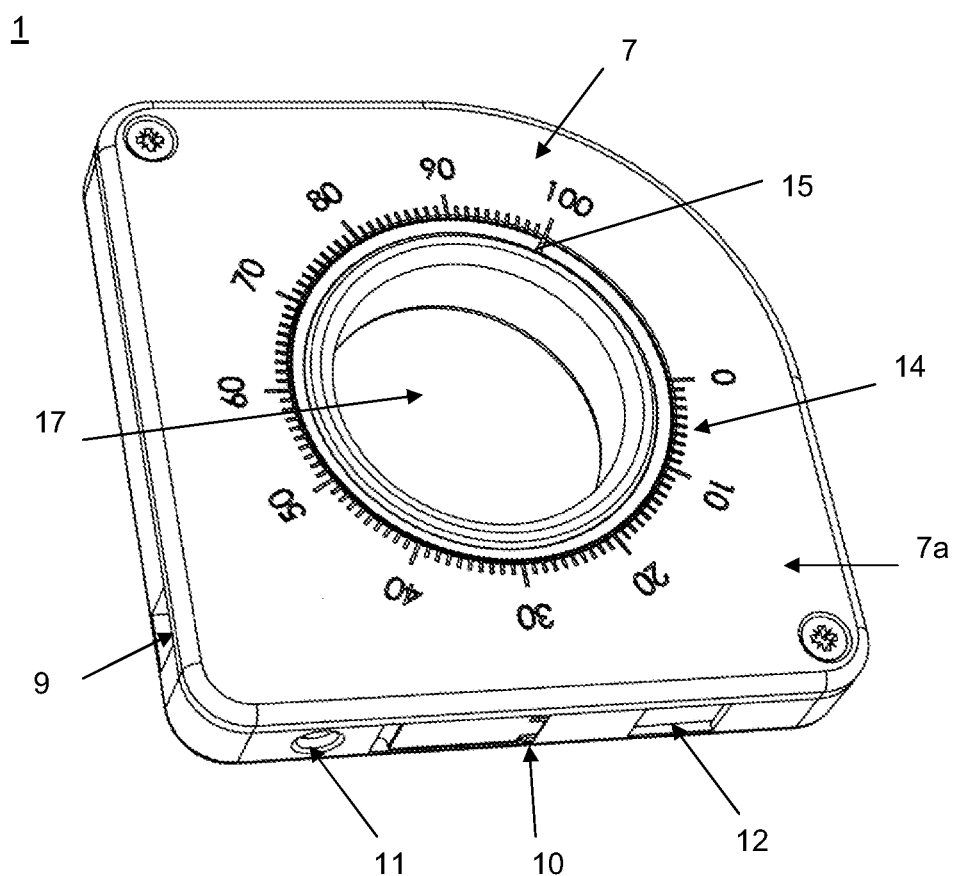
FIG. 1 illustrates a top view of a magazine according to the invention for chain components of a chain with radiation sources.
Figure 2:
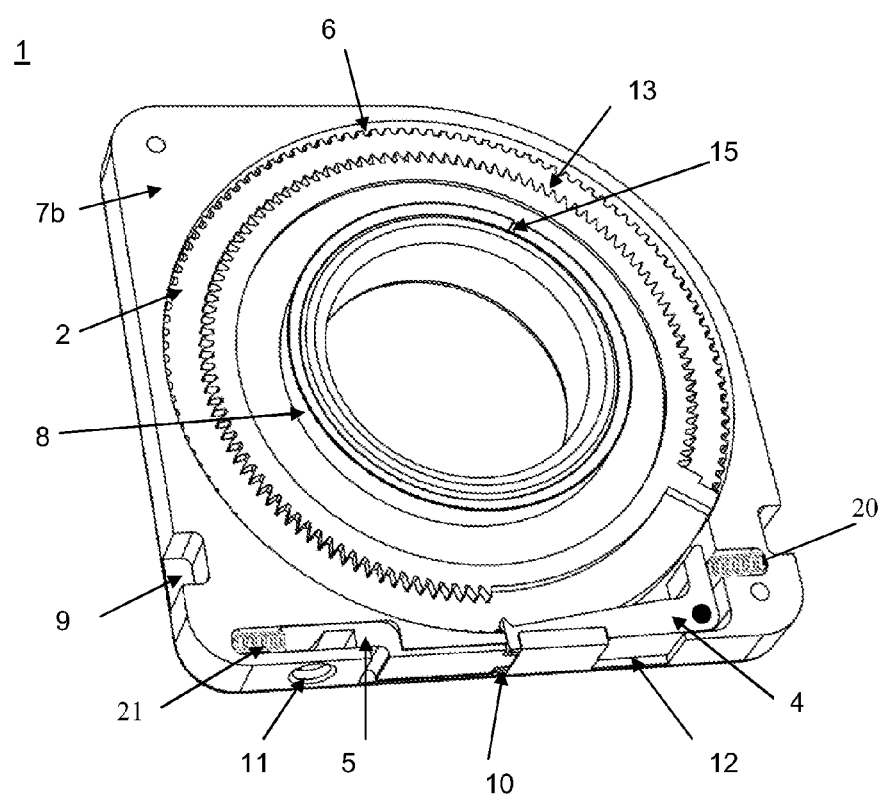
FIG. 2 illustrates a top view of a magazine according to the invention for chain components of a chain with radiation sources without a cover.
Figure 3:
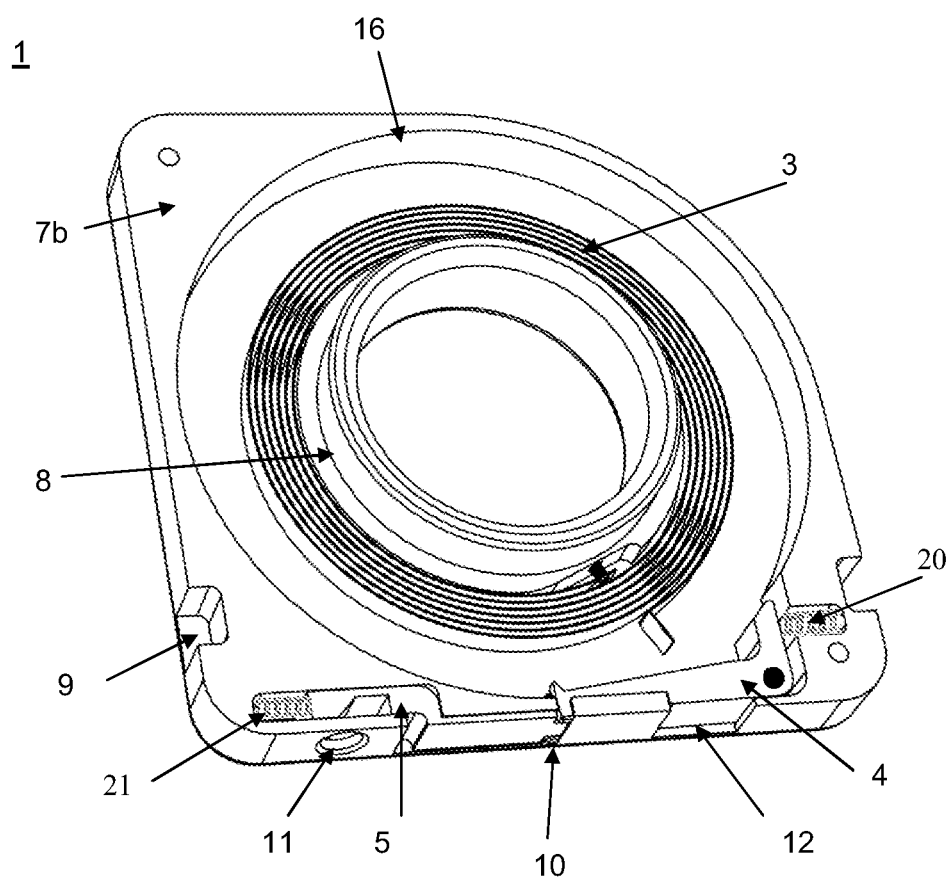
FIG. 3 illustrates a top view of a magazine according to the invention for chain components of a chain with radiation sources without a cover, without means for receiving chain components and without a sprocket.
Figure 4:
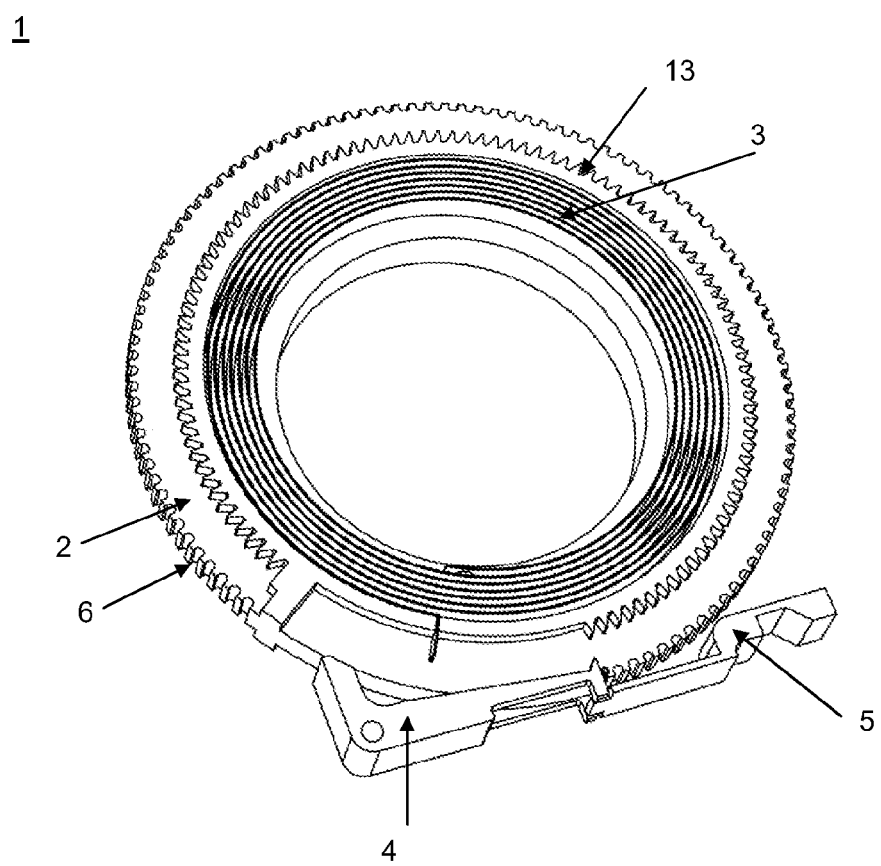
FIG. 4 illustrates core magazine components without the housing.
Figure 5:
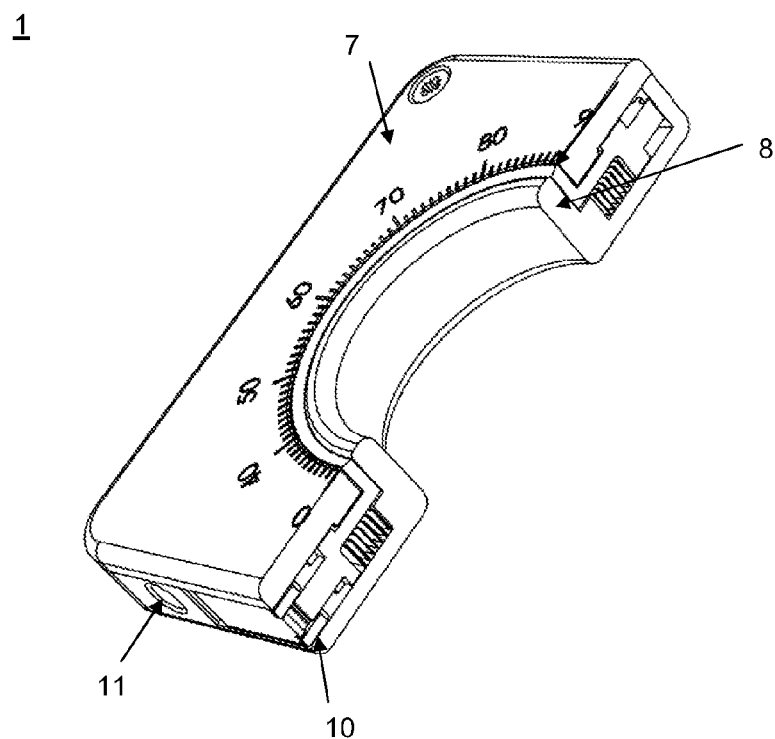
FIG. 5 illustrates a vertical section through the magazine of FIG. 1, FIGS. 6-11 illustrate the ejection mechanism according to the invention in various steps.

FIG. 1 shows a top view of a magazine (1) according to the invention for chain components of a chain with radiation sources. FIG. 2 shows a magazine without a cover (7a). In FIG. 3, a means for receiving chain components (2) and a sprocket (13) have been omitted. FIG. 4 shows the core components of the magazine without housing (7), and FIG. 5 shows a vertical section through the magazine of FIG. 1.

As shown in FIGS. 1 and 2, the inventive magazine (1) includes a housing (7) consisting of a cover (7a) and a housing shell (7b). The cover includes a display (14) for displaying the magazine's fill level in conjunction with a marking (15). The marking is preferably arranged on an interior bearing ring means used to receive chain components (2).

An encoding bore (11), an ejector (10) and a first opening (12) are arranged on the periphery of the magazine (1), preferably on the lower sidewall of the housing (7). Preferably, only one ejector or ejector opening (10) is provided so that the radiation exposure can be held to a minimum when using the radiation sources as chain components. Ejection thus occurs in the same or a parallel plane where the means for receiving chain components rotates. The chain components are ejected away from the magazine. After the chain component has left the ejector, there is no more contact between the magazine and the chain component. The encoding bore (11) and/or ejector (10) and/or the first opening (12) are preferably arranged separate from and below the means for receiving chain components (2), but in the same plane or in a parallel plane.

In a preferred exemplary embodiment, the magazine is configured for exactly one type of chain component, either for radiation sources or for spacers. Thus, it is impossible to confuse the ejected chain components.

An ejection lever (4) which is rotatably mounted in the housing (7) is arranged in conjunction with the first opening (12). The ejection lever (4) is actuated from the outside through the first opening (12). In the rest position, the ejection lever (4) closes the ejector (10) from the inside. The ejector (10) is also connected with a locking slider (5) which closes the ejector (10) to the outside by the force of a second tension spring (21). The locking slider (5) is translationally displaceable so that the ejector (10) is deblocked when the locking slider (5) is actuated. The locking slider (5) can be actuated via an opening (11) or the encoding bore (11) in order to deblock the ejector (10). Furthermore, the magazine has preferably, but not as a limitation, a central opening (17). As seen in FIG. 2, a circular means for receiving chain components (2), also referred to as a "seed depot" (2) when speaking of a magazine for radiation sources, is inserted and rotatably supported in the rear housing shell (7b). The means for receiving chain components (2) includes radially arranged recesses (6) which are designed to receive chain components, such as radiation sources (19) or spacers (18), and prevent them from a falling out. The recesses (6) are preferably designed to match the shape of the chain components. It is particularly preferable that the recesses (6) have a semicirclular shape and are provided on the circular edge along the periphery of the means for receiving chain components (2). In other words, the means for receiving chain components (2) resembles a gear wheel, but, has recesses (6) on its outer edge instead of teeth. A tension spring (3), preferably a constant-force spring (3), enables advance of the means for receiving chain components (2) concentrically with its center. Thus, no external driving force of the magazine is required for ejecting a chain component. The magazine can be completely sterilized. Only an external impulse on the ejector lever is required to eject a chain component so that the drive can be operated independently in the interior. A material wall from the housing (7) serves as the bearing surface in form of an interior bearing ring (8) for the means for receiving chain components (2). The interior bearing ring (8) is preferably formed around the opening (17). Furthermore, a sprocket (13) which preferably has a smaller diameter than the means for receiving chain components (2) is arranged on the means for receiving chain components (2). The sprocket (13) is preferably operatively connected to the means for receiving chain components (2) or is directly connected to the constant-force spring (3) and is also rotatably supported in the housing (7). The sprocket (13) is connected with the means for receiving chain components (2) with a rotation lock, which is designed to limit the advance of the constant-force spring (3) during ejection so that only a single chain component can be ejected at one time. Preferably, the sprocket (13) and means for receiving chain components are formed in one piece.

Starting from the center of the magazine (1) proceeding towards the outside, the magazine (1) consists of a central opening (17), an interior bearing ring (8), the sprocket (13), the means for receiving chain components (2) and a boundary (16) of the means for receiving chain components (2). In the present exemplary embodiment, the sprocket (13) and the means for receiving chain components (2) are embedded into a depression of the rear housing shell (7b).

The inner wall (16) of the depression (see FIG. 3) serves to limit the means for receiving chain components (2). The distance between the wall (16) of the depression, or more generally, between the boundary (16) of the means for receiving chain components (2) and the means for receiving chain components (2) itself, is sized in such a way that the chain components can be are guided and held captive in the recesses (6). The chain components are hereby guided on a circular path towards the ejector (10). The tension spring (3) is supported below the means for receiving chain components (2), as seen in FIG. 3.

As described below, the ejection lever (4) inhibits the spring (3) and therefore the means for receiving chain components (2). Inhibition of the spring (3) and the means for receiving chain components (2) allows only the release of a single implant or chain component from the magazine for each magazine actuation. Inhibition takes place, on one hand, by positive locking of the first implant on the ejector lever (4) and, on the other hand, by the cyclical engagement of the upper sprocket (13). The ejector lever (4) also supports release of the implant by actively pushing the implant into a working channel. The ejector lever (4) is preferably springily supported and is actuated using a corresponding lever mechanism in the loading device (101) described below. The implants are released from the opening (10) at the magazine base into a working channel. The magazines (1) are preferably mechanically encoded and color-coded. The color-coding can be performed by coloring the means for receiving the chain components (2), which represents the moveable component of the scale. The number of spent radiation sources and spacers can be read directly on the magazines.

The following is a description of the magazine, exemplified using a radiation source magazine. This, however, is not a limitation. The discussion also applies to spacer magazines, unless anything to the contrary is explicitly mentioned.

To assemble the magazine (1), the tension spring (3) is first mounted to the rear half of the housing and is then inserted together with the means for receiving chain components (2) in the rear housing shell (7b). Subsequently, an ejector lever (4) and a locking slider (5) are used and tensioned, preferably using tension springs 20 and 21, as shown in FIG. 3. Here, the ejector lever (4) is rotatably mounted via a pin and the locking slider (5) can be translationally displaced in a groove in the housing shell (7b).

After assembling the magazine (1) without the cover (7a), the radiation sources (19) (or the spacers (18)) are positioned parallel to the axis of the means for receiving chain components (2) in the semi-circular recesses (6) on the front side of the means for receiving chain components (2). Before loading the means for receiving the chain components (2), the tension spring (3) must be tensioned, preferably using a constant-force spring (3). This is done by rotating the means for receiving chain components (2) in the tensioning direction of the tension spring (3). Inserting the first radiation source (19) prevents the tension spring (3) from relaxing. The additional radiation sources (19) are subsequently inserted. In the subsequent operation of the magazine (1), the respective first radiation sources (19) serve (before their release) as a blocking element or as means to prevent the tension spring (3) from relaxing. After the magazine (1) is filled, a cover (7a) is applied. An inner bearing ring (8) of the means for receiving chain components (2) is widened and serves, when provided with a marking (15), in conjunction with the magazine cover (7a), as a content indicator for the radiation sources (19) or spacers (18) remaining in the magazines.

With the exception of the locking slide (5) and the respective milled-out portion in the rear housing shell (7b), the magazine (1) for storing the spacers (18) is identical to the radiation source magazine. Therefore, assembling and filling both types of magazines are done similarly. The locking slider (5) can also be arranged in the spacer magazine. However, this is not absolutely necessary because the spacers are not radioactive. The locking slider (5) from the radiation source magazine serves to shield the radiation towards the outside before the magazine is inserted into the device (101) for filling.

At least one, preferably both, of the narrow sides of a magazine (1) are provided with locking grooves (9). These serve, after installation of the magazine (1) into a device (101) for assembling radiation sources, to hold them captive in the device as well as a positioning aide for a working channel in device (101).

In the center region of the bottom surface of the radiation source magazine there is an opening for ejecting the implants (10). The side on one side of this opening (10) is provided with an encoding hole (11). When installing the radiation source magazine into a device for joining radiation source chains (101), the locking slider (5) is displaced by an encoding bolt in the device (101) so as to release the ejection opening (10). This function is preferably not implemented in the spacer magazine, since the locking slide (5) is supposed to prevent exposure of the operator to radioactive radiation from the radiation sources (19). This is not necessary for the spacers (18), since these are not radioactive. Of course the slider (5) can still be provided.

Figure 6:
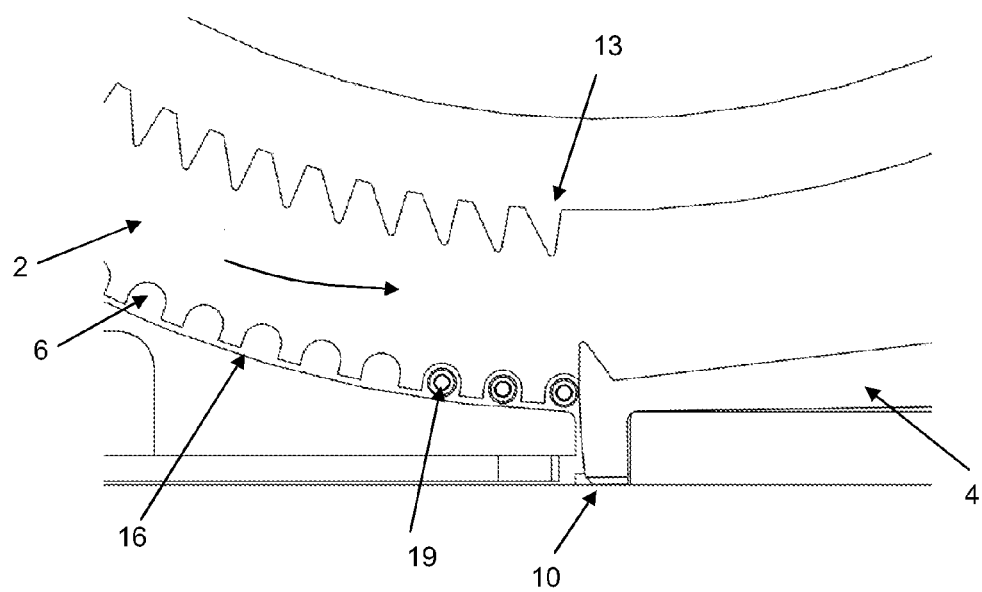
Figure 7:
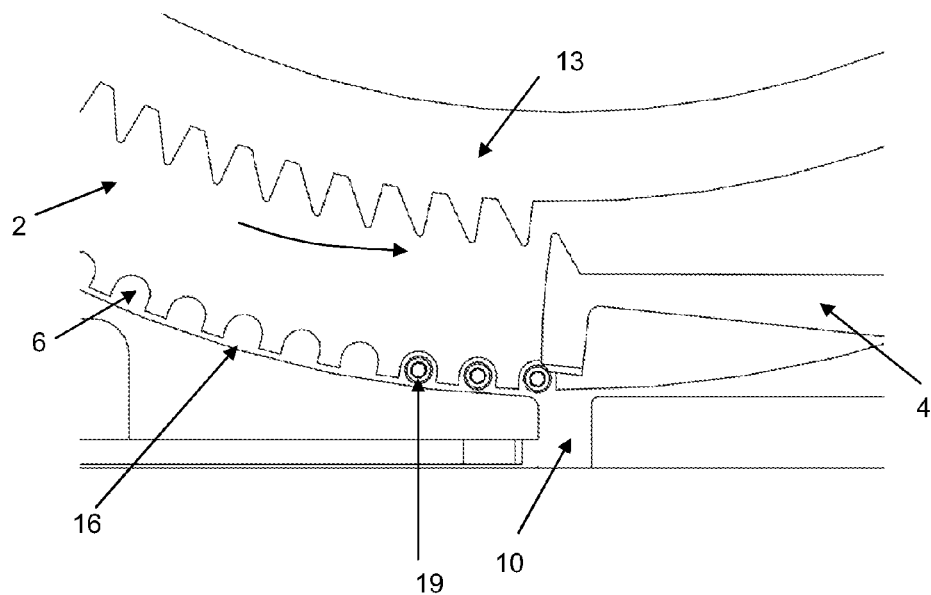
Figure 8:
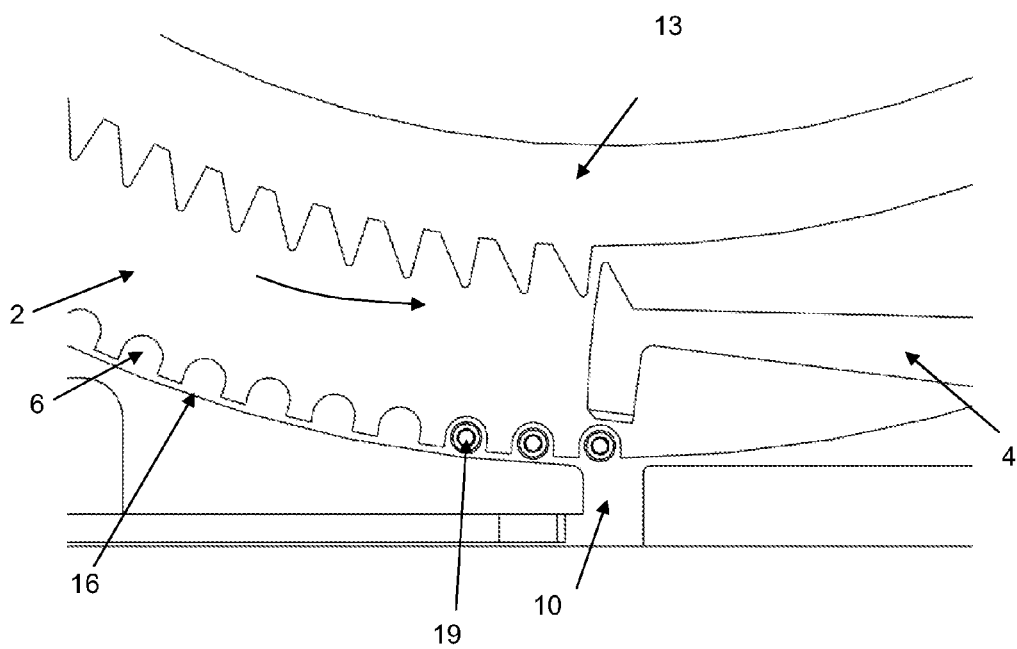
Figure 9:
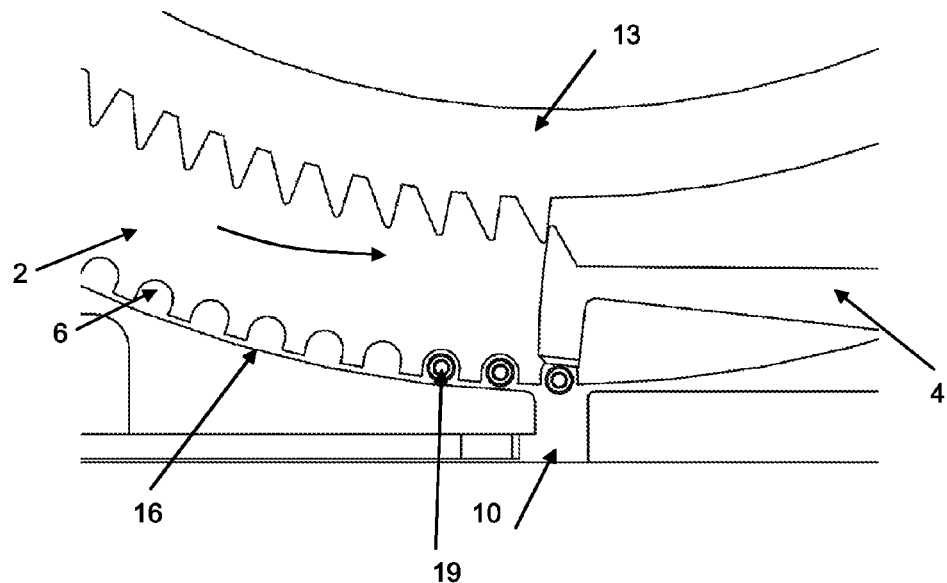
Figure 10:
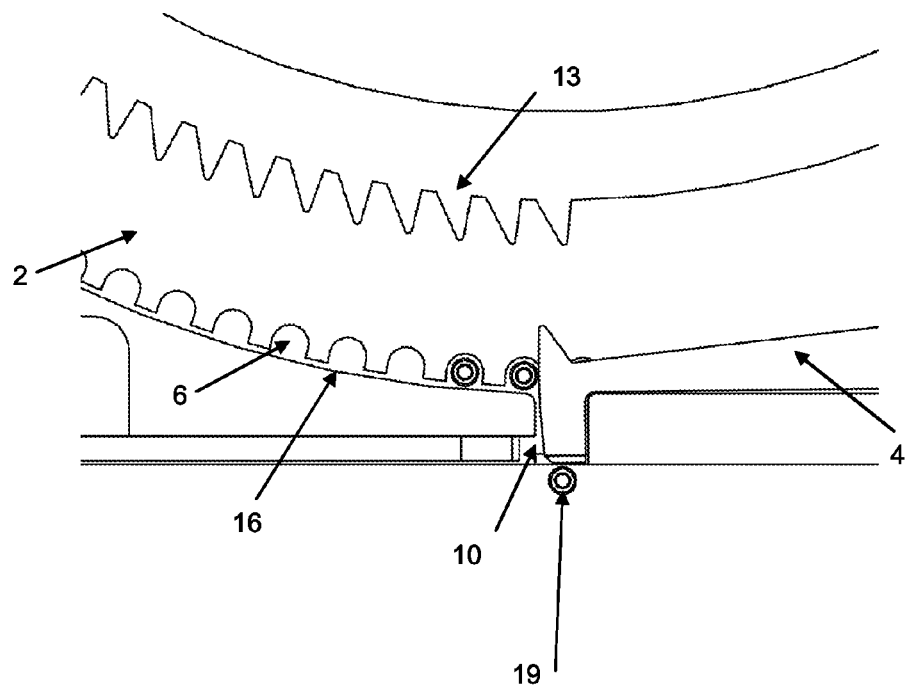
Figure 11:
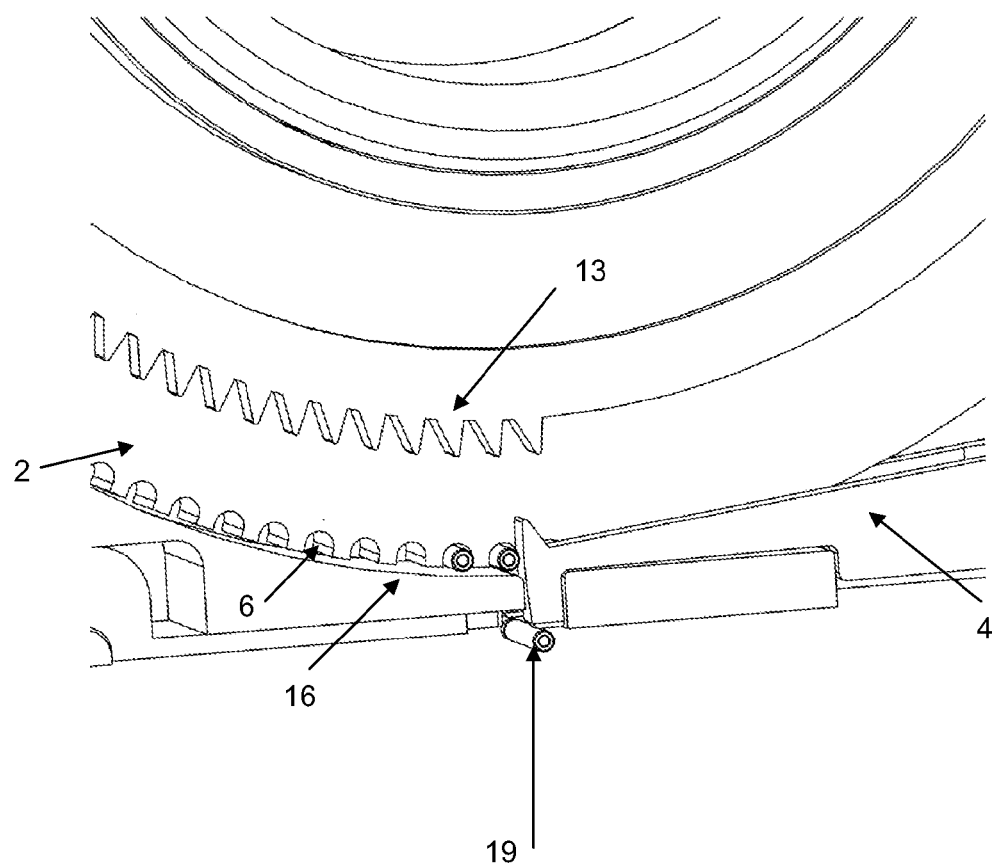
Figure 12:
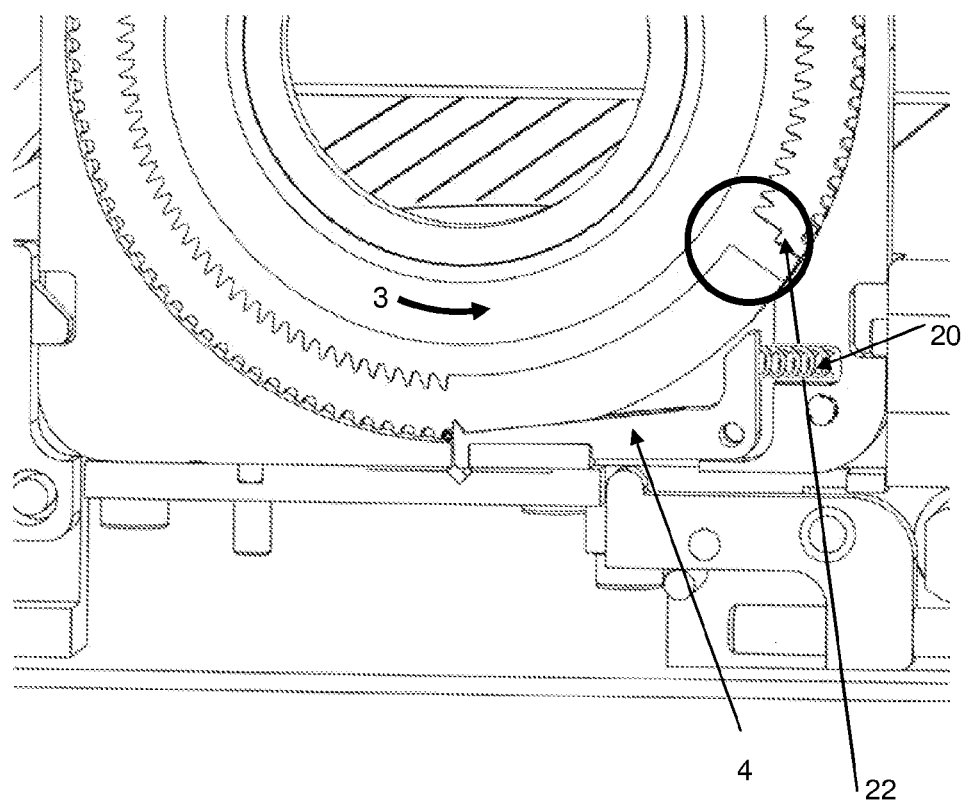
FIG. 12 illustrates the blocking mechanism according to the invention in the magazines, to be amended to FIG. 13 A illustrates one embodiment of joinable spacers and radiation sources.

The ejector lever (4) can be operated via a corresponding lever mechanism (113) in the device (101) through a second opening (12) on the other side of the ejection opening (10). The ejection mechanism is illustrated in individual steps in FIGS. 6 through 11. Initially, the ejection opening (10) is physically blocked by the ejector lever (4), as illustrated in FIG. 6. In this position, the ejector lever (4) does not engage with the sprocket (13). A single radiation source (19) or a spacer (18) are ejected from the magazine (1) by operating the outer surface of the ejector lever (4), which causes the ejector lever (4) to slide up towards the first radiation source (19) or the first spacer (18) (FIG. 7). The first radiation source (19) or spacer (18) loses its blocking function depicted in FIG. 6, the means for receiving chain components (2) moves, driven by the tension spring (3), concentrically to the central opening (17) or the center of the magazine (1). However, this motion is blocked during further movement by the engagement of the ejector lever (4) with the gears of the upper sprocket (13) of the means for receiving chain components (2) (FIGS. 8, 9). This rotation of the means for receiving chain components (2) pushes the first radiation source (or spacer), and only it, into a position located above the ejection opening (10) (FIG. 9). The first radiation source is then released downward towards the rear via the ejector lever (4), preferably into a working channel (not shown) below the ejection opening (10) for the assembling the chain components (FIGS. 10 and 11). After operating the ejector lever (4), the ejector lever returns to its previous position and blocks the ejection opening (10) again, as shown in FIG. 6. This again prevents further rotation of the means for receiving chain components (2) due to the abutment of the next first radiation source (19) or the next first spacer (18) on the ejector lever (4) (FIG. 11). This mechanism incrementally rotates the means for receiving chain components (2) and makes a single ejection of the radiation source (19) or spacer (18) into a working channel possible. Release of the lever 4 for magazine operation of empty magazines (1) is not possible. This is illustrated in FIG. 12. An arrow shows the rotation direction of the means for receiving chain components (3). The last magazine implant is arranged at the location indicated with a circle. After the last implant is ejected from the magazine, the lever (4) falls into the circled trough of the blocking element (22) forced by the tension spring (3) and the lever spring, and the first compression spring (20). The blocking element (22) does not offer room for movement of the lever (4). Operation of the buttons (113a) of the lever mechanism (113) for ejecting chain components (see FIG. 18) causes an excursion of the lever (4) via a lever mechanism (113). However, because this movement is blocked, operation of the buttons (113a) is also blocked with an empty magazine.

Figure 13A:
FIG. 13 B illustrates a second embodiment of joinable spacers and radiation sources.
Figure 13B:

FIG. 13 shows spacers (18) and radiation sources (19) configured for assembly. FIG. 13a shows an external, longitudinal cross-section of the spacers (18) and radiation sources (19). The radiation sources (19) have an interior radioactive core, illustrated as a rectangle in FIG. 13a. The radiation sources (19) and spacers (18) have ends configured for joining or assembly into a chain. Two spacers (18) or two radiation sources (19) can also be joined together. The spacers (18) or radiation sources (19) preferably each have male ends (right) and female ends (left). The chains can be freely assembled due to the design of the radiation sources (19) and spacers (18).

Figure 14:
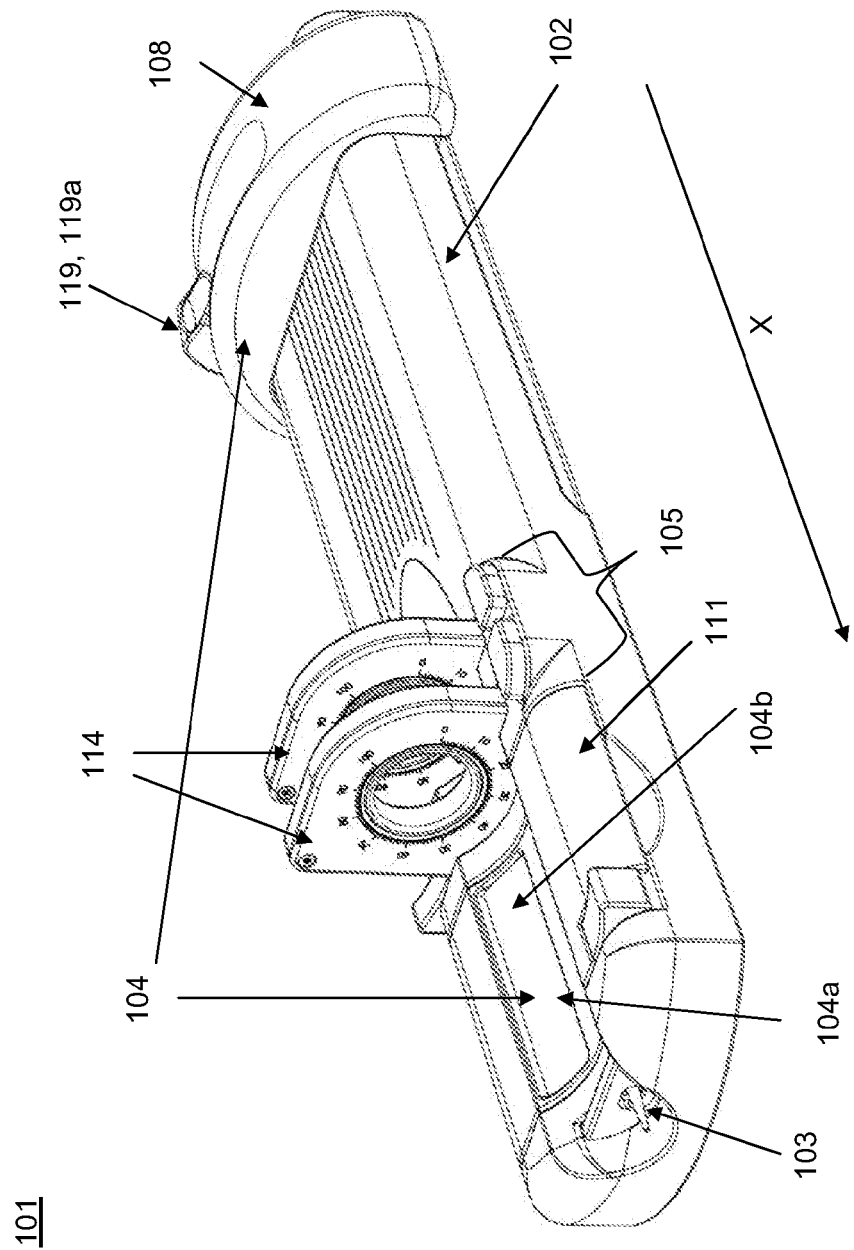
FIG. 14 illustrates a perspective view of the inventive device for joining and assembling chains containing radiation sources.

FIG. 14 shows a perspective view of a device (101) according to the invention for joining and assembling radiation chains with radioactive radiation sources, preferably operated with the magazines 1 described above.

Figure 15:
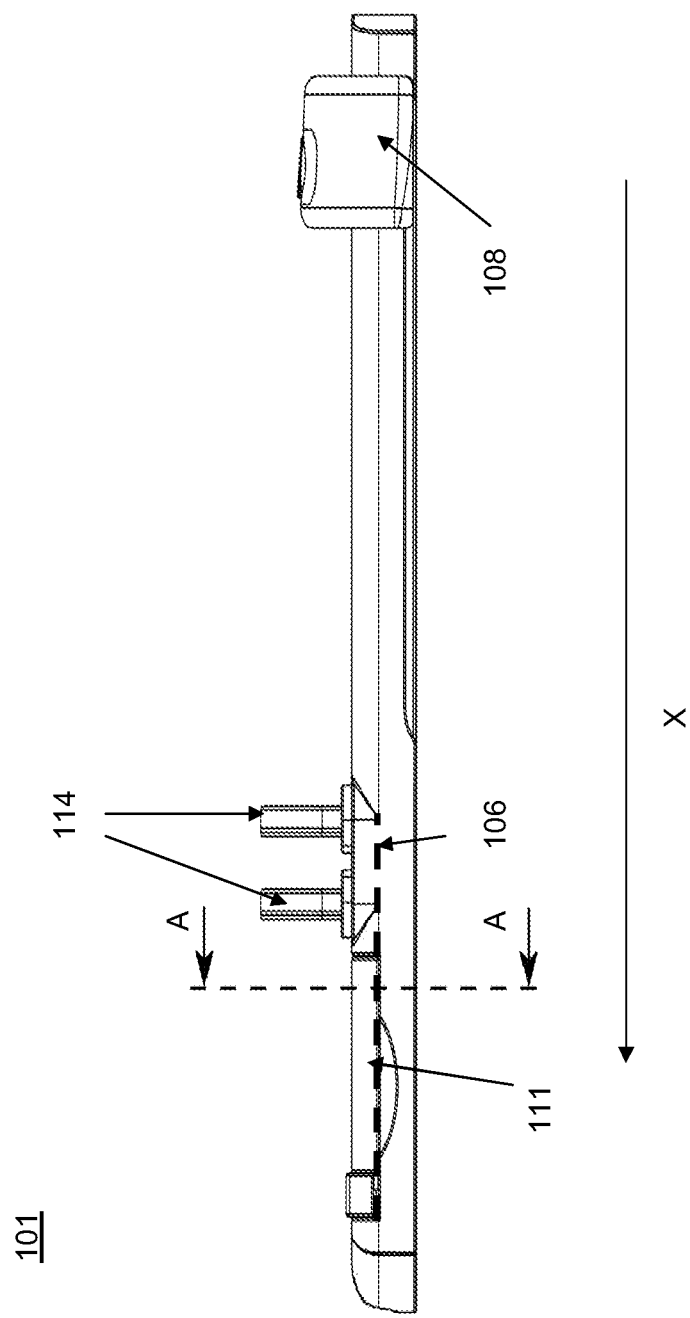
FIG. 15 illustrates a side view of the inventive device for joining and assembling chains of FIG. 14.
Figure 16:
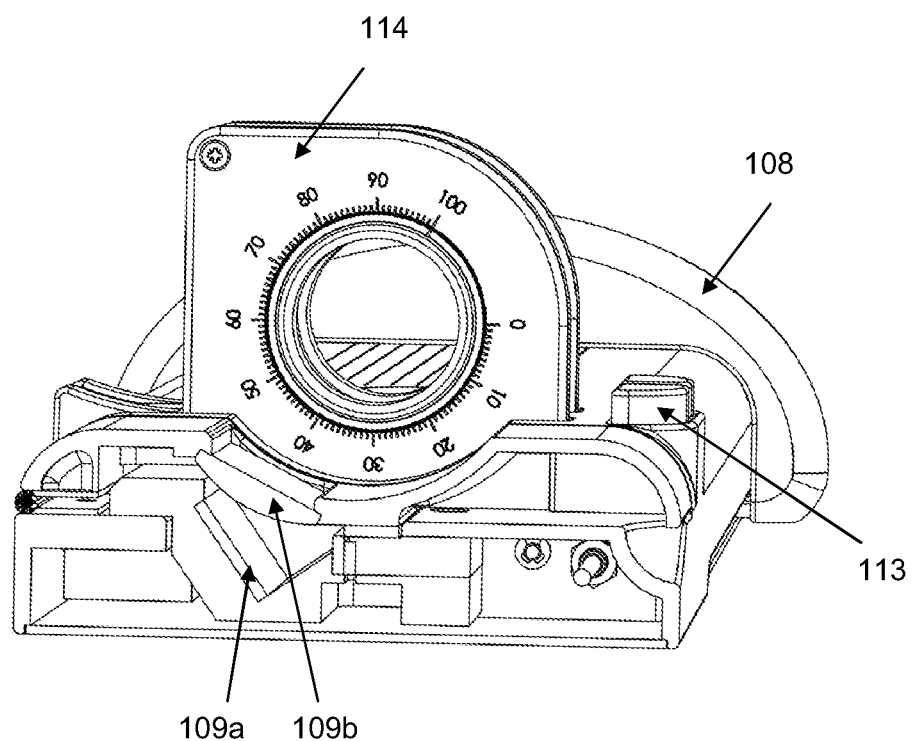
FIG. 16 illustrates a perspective cross-section of the inventive device along the line A- A in FIG. 15, as seen in the direction opposite to the arrow in FIG. 15.
Figure 17:
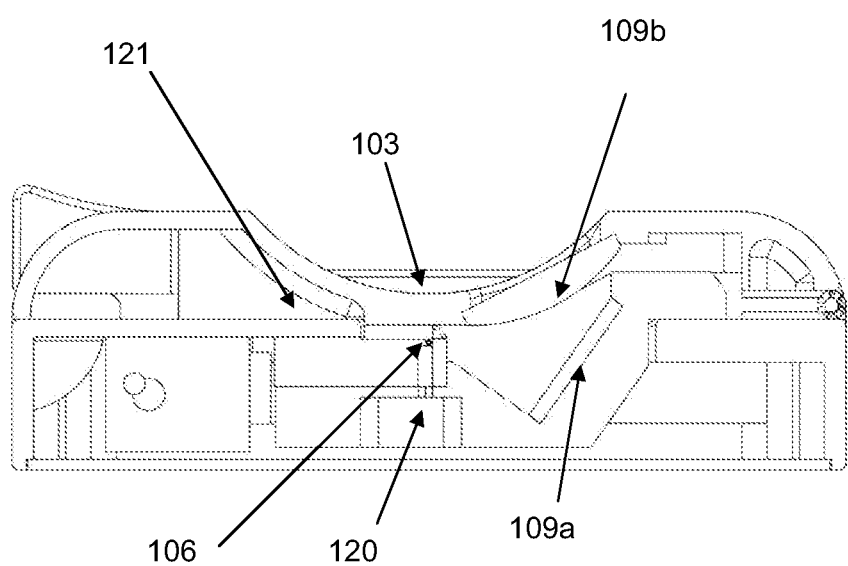
FIG. 17 illustrates a cross-section through the inventive device along the line A-A in FIG. 15, as seen in the direction of the arrow in FIG. 15.
Figure 18:
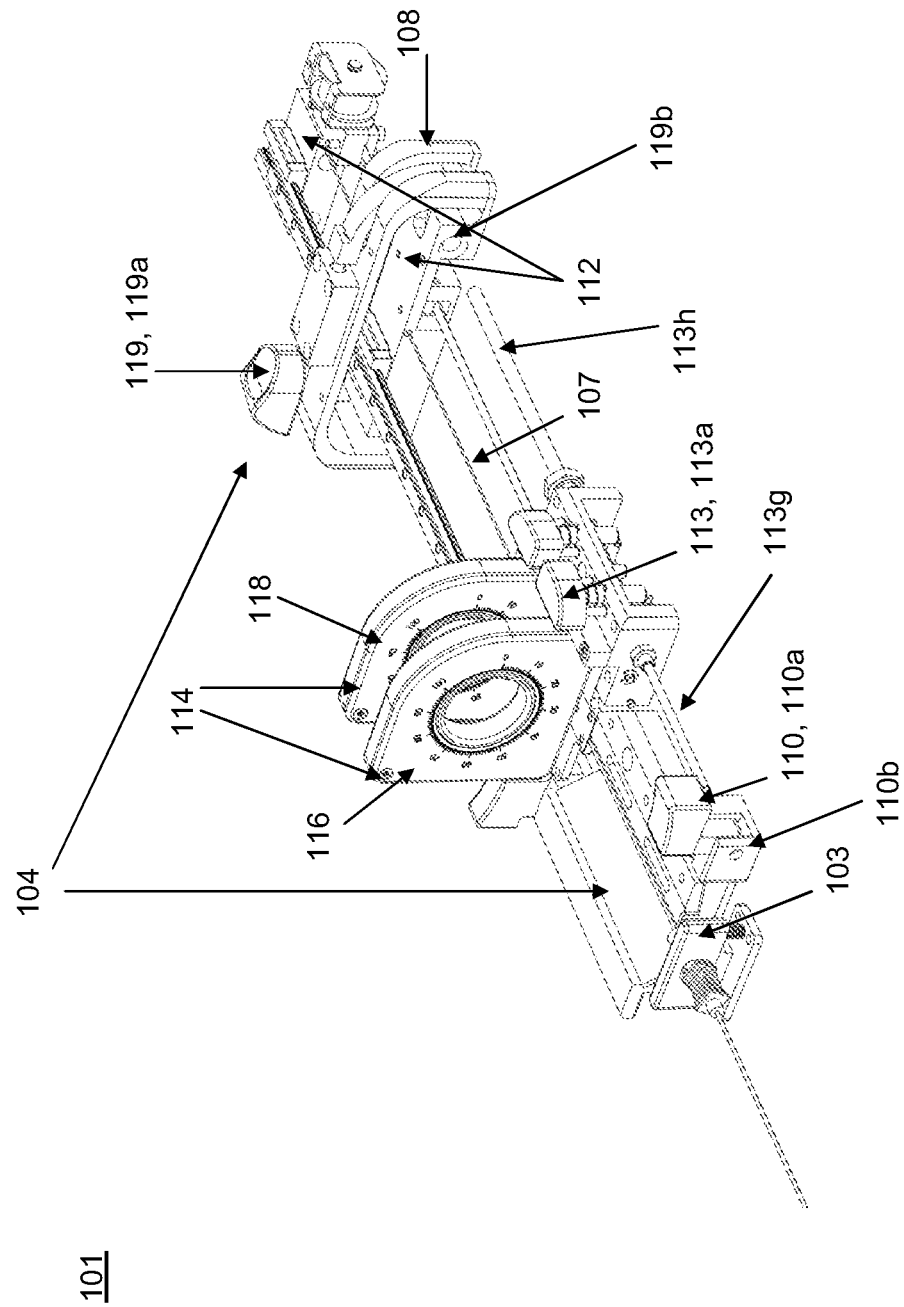
FIG. 18 illustrates a first view of the inventive device without housing.
Figure 19:
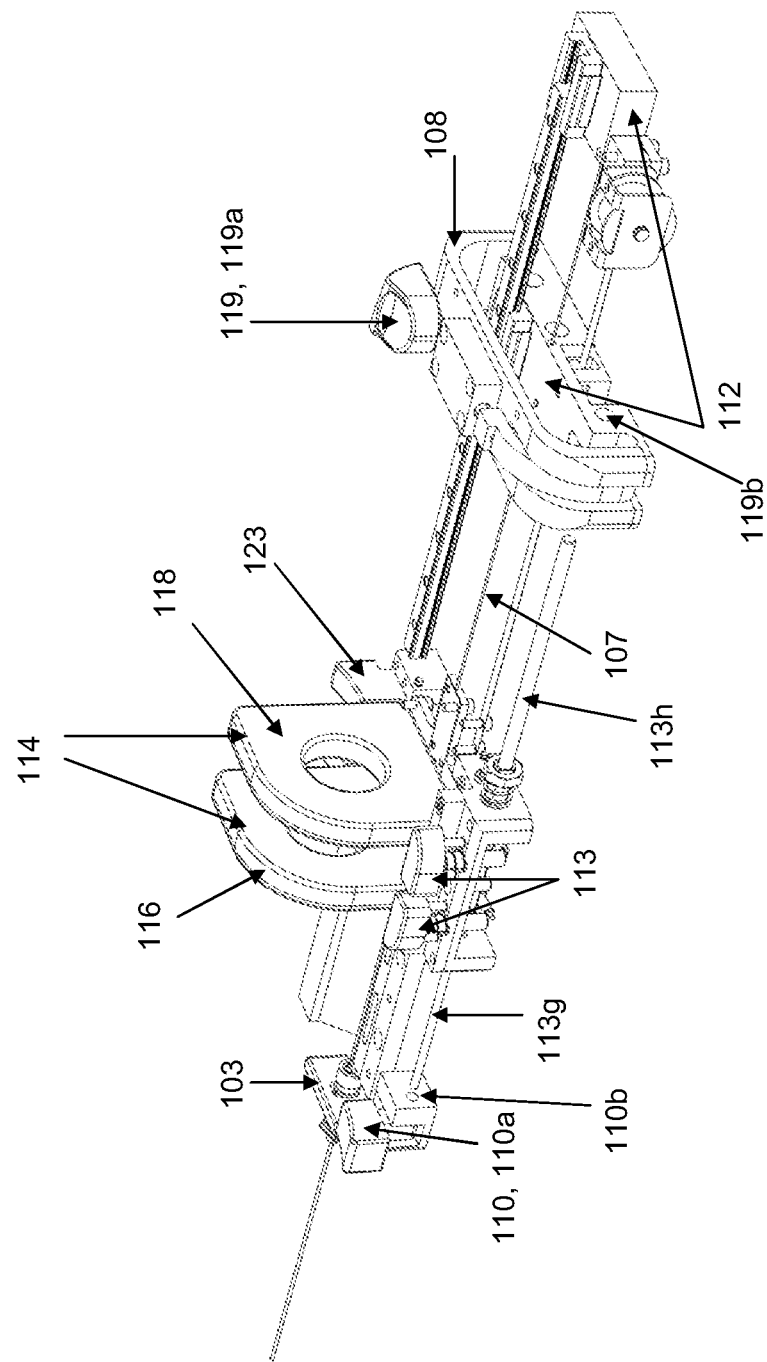
FIG. 19 illustrates a second view of the inventive device without housing.
Figure 20:
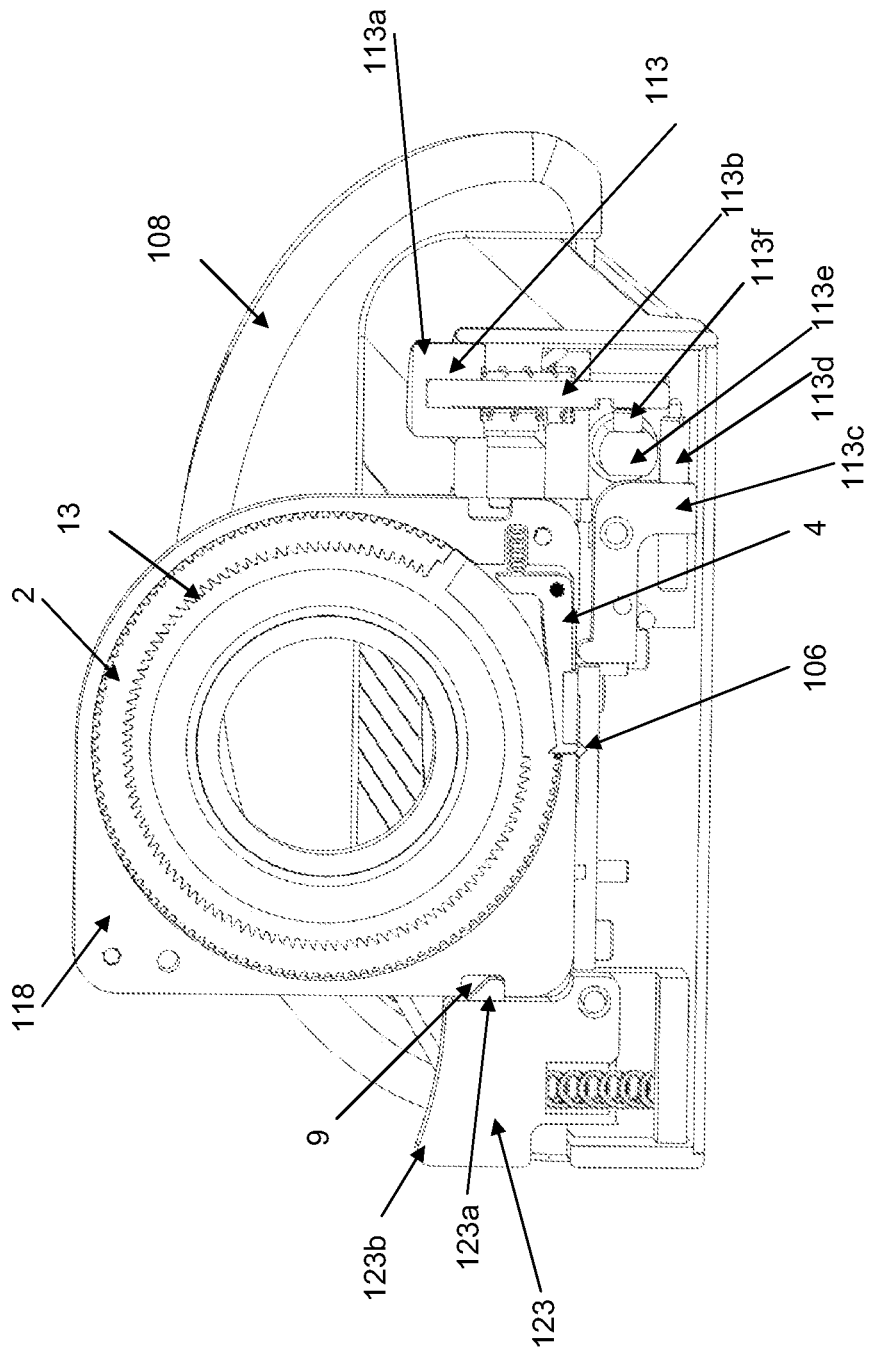
FIG. 20 illustrates a cross-section of the joining device through a spacer magazine.
Figure 21:
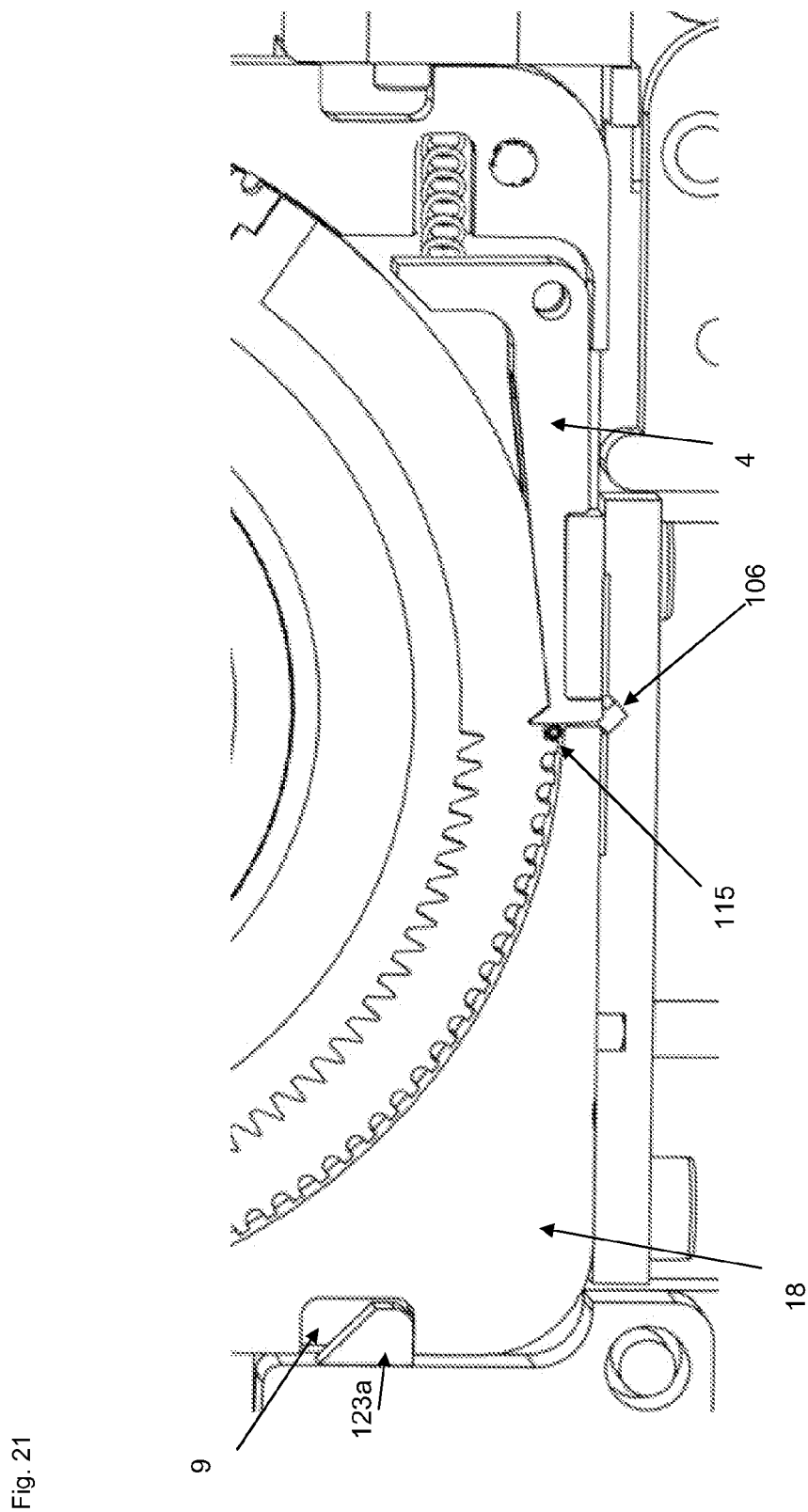
FIG. 21 illustrates an enlargement of FIG. 20 in the lower section of the spacer magazine.
Figure 22:
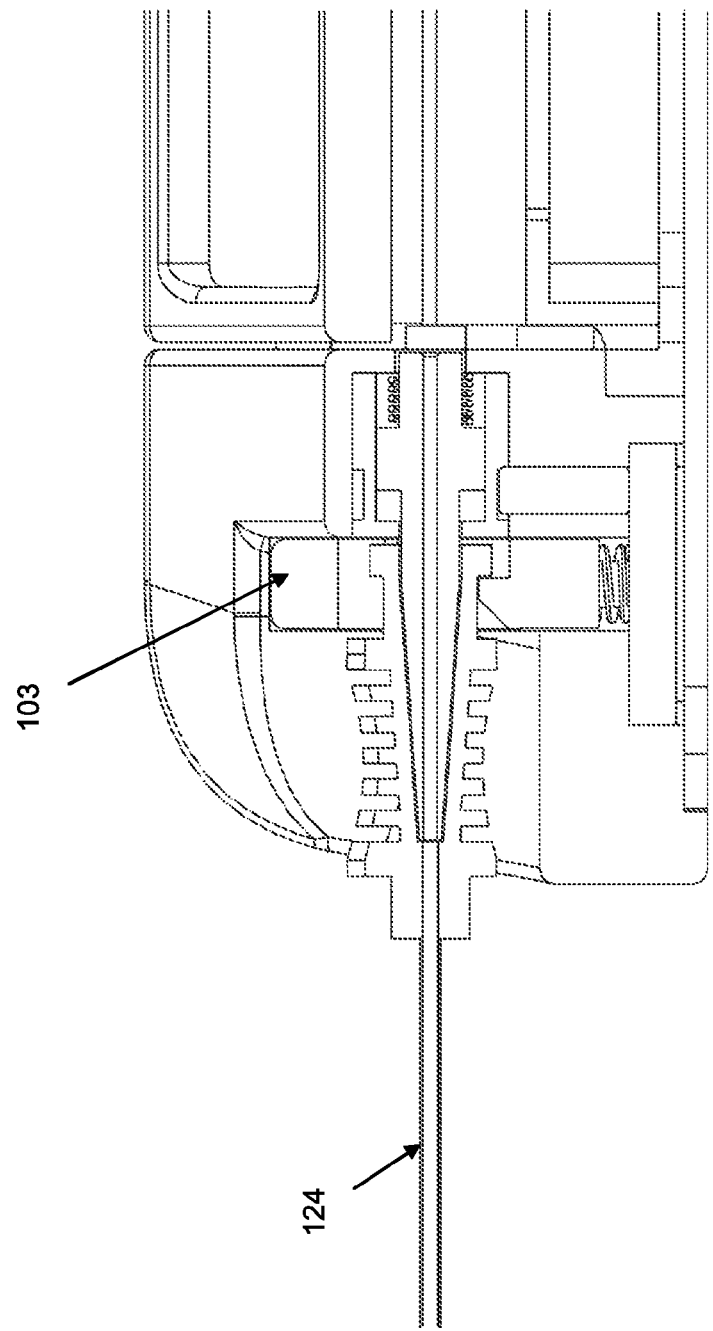
FIG. 22 illustrates a longitudinal section through the front section of the inventive joining device in the needle holder area.

FIG. 15 shows a side view of the device according to the invention for joining and assembling the radiation chains in FIG. 14. FIG. 16 shows a perspective cross-sectional view of the device according to the invention along the line A-A of FIG. 15, seen in the direction opposite to the arrows in FIG. 15. FIG. 17 shows a cross-section of the device according to the invention along the line A-A of FIG. 15, seen in the same direction of the arrows in FIG. 15. FIG. 18 is a first view of the device according to the invention without a housing. FIG. 19 is a second view of the device according to the invention without a housing. FIG. 20 shows a cross-section of the device for joining through a spacer magazine. FIG. 21 illustrates an enlarged view of FIG. 20 in the lower region of the spacer magazine. FIG. 22 shows a longitudinal section through the front region of the device according to the invention for joining in the region of the needle holder.

The device (101) according to the invention consists of a housing (102), a needle holder (103), a joining and observation unit (104) and a loading unit (105), as shown in FIG. 14. Magazines (114) for chain components are installed in the loading unit. The joining and observation unit (104) preferably includes a joining region (104a), where the chain components are joined, as well as a observation region (104b) for checking the arrangement of the chain components. In a preferred exemplary embodiment, the joining region (104a) can be reached from the outside via a flap (111). The needle holder (103) is arranged on one end of the device, whereas a handle (108) is arranged on the other, as described in more detail below. A third lock (119) configured as a button element is arranged on the handle (108). The magazines (114) and the joining and/or observation regions (104a, 104b) are located between the handle (108) and the needle holder (103).

It is an object of the device (101) to assist with releasing radioactive radiation sources (115) and inactive spacers (117) from corresponding magazines (114), to join the implants (see FIG. 13) or chain components (115, 117) containing plug connections in form of a chain, and to then fill with them the needles (124) attached to the device (101) (see FIG. 22).

A central element of the aforedescribed device (101) is the working channel (106), which, as shown in FIGS. 15, 17, 19, and 20, extends along the X axis or a longitudinal axis of the device (101). The working channel (106), as seen from the handle, preferably starts closely before the magazine holders or, alternatively, exactly below the ejection opening of the magazine (114) closest to the handle and ends at the needle holder (113). The start of the working channel (106) closely before the magazine brackets enables better steering of the mandrel (107), as described later. The various units are arranged around the working channel (106), supported by the housing (102). The housing (102) supports and protects the other functional units of the device (101). FIGS. 14 and 15 show from right to left the handle (108), the magazines (114) with the loading unit (105), the joining and observation region (104a, 104b), and the needle holder (103).

The joining and observation unit (104) includes the working channel (106) and has a mandrel (107) (see FIG. 18 or 19), which is linearly guided by an external handle (108) in the working channel (106) as well as a minor-lens unit (109) (see FIG. 17) for viewing the implants in the joining region (104a). The mandrel (107) transports, via the handle (108) which can be laterally displaced by the user, the radiation sources (115) or spacers (117) released from the magazine from the section of the working channel (106) below the magazines (114) into the joining region (104a). The configuration in the joining region (104a) can advantageously be checked via the observation unit (104b). After the desired configuration of implants has been established, the implants are pushed together in the joining region (104a) with the help of the mandrel (107) and joined to form a seed-spacer chain. As an abutment, a first lock (110), which includes a button (110a), blocks during the joining process a transition from the working channel (106) to the needle holder (103). After joining, the first lock (110) is opened, thereby allowing the ejection of joined implant chains via the needle holder (103) into the needle (124) (see FIG. 22). The first lock (110) is thereby preferably arranged in front of the needle holder (103) and behind the observation region (104b), but can also coincide with the needle holder (103).

The manually operable needle holder (103) consists of a locking device and a needle adapter which guides the joined implant chains into the attached needle (124). The locking device of the needle holder holds and secures the needle (124) captive during filling.

A lens-mirror system (109) allows for indirect and thereby radiation-protected visual contact with the implants or chain components. Via a flap (111) in the observation unit (104b), direct access to the working channel (106) is possible, in order to perform possible corrections to the seed-spacer configuration. For short-term, interim storage of the radiation sources or spacers during a correction, two trough-shaped storage places are available below the radiation-protected valve (111).

Both magazines (114) are latchingly fixed during operation of the device (101) via a safety mechanism (123), as shown in FIG. 20, and held captive. The safety mechanism (123) includes a projection engaging in the locking groove (9) of a spacer magazine (118). The magazines (114), however, can be unlocked and removed by operating a corresponding release lever. An swap of magazines (114) in their designated locations is not possible via mechanical encoding. Preferably, the radiation source magazine (116) has encoding different from the encoding of the spacer magazine (118). The encoding can be carried out via an encoding bolt that engages with a corresponding encoding opening (11) of the magazine. The encoding of the radiation source magazine (116) additionally displaces an aforementioned locking slider (5) when the magazine (116) is inserted. This provides additional protection from radiation exposure during handling and during transport of the magazine (116) prior to installation into the device (101). The locking slider (5) closes again after removal of the radiation source magazine (116).

To prevent damage to the implants from excessive force when joining the implants the flange unit (104) is provided with a magnetic coupling (122). The carriage (112) guiding the handle (108) and the mandrel (107) is constructed in two parts, as shown in FIGS. 18 and 19. Both parts separate when the holding force of the magnetic force is exceeded.

The charging unit (105) includes the slots for a spacer magazine and a radiation source magazine (118, 116) as well as a mechanical lever mechanism (113) for releasing the implants. After inserting a magazine (114) and operating a corresponding button (113a) in the lever mechanism (113), an implant is released from the magazine into the channel (106) below. The lever mechanism (113) for each magazine (114) has a lever mechanism button (113a), preferably slidingly supported, a button rod (113b) with a crosswise groove, whereby the button rod (113b) is preferably a springily supported and beveled one-sided towards the first pressure spring piece (113d). Furthermore, the lever mechanism (113) includes a lever (113c) which is rotatably and springily supported in the housing with a first pressure spring piece (113d) and a push rod (113e) translationally guided transversely to the button rods (113b), with a corresponding second pressure spring piece (113f) for each lever mechanism, as well as a first extension (113g) of the push rod and a second extension (113h) of the push rod.

The lever mechanism (113) will now be described in more detail with reference to FIGS. 18-20. By pressing on the button (113a), the button rod (113b) which is preferably slideably guided on both sides is moved downwards (see FIG. 20), where it presses with its free end onto the springily supported pin of the first pressure spring piece (113d), thereby pressing the pressure spring piece (113d) downward. Because this pressure spring piece (113d) is directly connected to the lever (113c) which is rotationally supported in the housing, button rod (113b) transfers the motion directly to the lever (113c). The lever (113c) thereby lifts the end facing the pressure spring piece (113d), which engages with the magazine disposed above and thereby initiates the release of the implant.

In order to fix the lever mechanism button (113a) in the lower position after actuation, a second pressure spring piece (113f) of the push rod (113e) latches in a crosswise groove of the beveled button rod (113b). Simultaneously, the springy pin of the first pressure spring piece (113d) of the lever (113c) slides along the beveled button rod (113b). Since the lever (113c) is springily supported, it return to its original position. It is the purpose of this mechanism to temporarily secure the button (113a) in the pressed position after actuation, for safety reasons, while allowing the lever (113c) to return to its initial position after activating the magazine (114).

As can be seen in FIGS. 18 and 19, the push rod (113e) is elongated on both sides of the lever mechanism (113), with a first extension (113g) and a second extension (113h). The first extension (113g) of the push rod (113b) is arranged between the magazines (114) and the first lock (110) and can engage in an opening (110b) of the first lock (110) and open the lock button (110a) of the first lock (110). The second extension (113h) of the push rod (113b) is arranged between the magazines and the handle (108) and engages in an opening (119b) of the third lock (119).

If implants (115, 117) were released below the magazine (114) and the buttons (113a) remain in the lower placement, then the handle (108) must first be pushed in the X direction. If the handle is pushed in the X-direction and the third lock (119) is closed, then the user pushes the third lock (119) against the one second extension (113h) with the handle (108) and hence against the push rod (113e). In this state, the second extension (107) is fixed in the opening (119b) of the third lock (119) and is displaced with the handle (108). The second pressure spring pieces (113f) of the push rod (113e) are then pushed out of the crosswise grooves of the button rod (113b), thereby unlocking the buttons (113a). Since movement of the handle (108) also moves the mandrel (107), unlocking the button (113a) automatically displaces the implants from the space below the magazines.

If the third lock (119) is open, then the handle (108) and the mandrel (107) can be displaced in the X-direction without being delimited by the third lock (119) and the second push rod extension (113h). This position is used to join the implant chains and later push them into the needle (123). However, in this position of the third lock (119), the buttons (113a) cannot be unlocked again.

If the first lock (110) was opened to push the implant chain into the needle (123) after joining, the implant chain is fixed in this position to prevent damage to the chain when the lock (110) falls back. It is only closed again by an impulse from the first extension (113g) of the push rod (113e) via the opening (110b), if the carriage with the third lock (119) displaces the second extension (113h). In a closed state, the first lock (110) serves as an abutment for joining the implant chain from the individual implants.

With the lever mechanism (113), ejection of two chain components on top of one another can be prevented. However, the buttons (113a) of the different magazines (114) can also be released simultaneously since they are arranged with a horizontal spacing above the working channel (106). Advantageously, this enables quicker assembly by simultaneous (or within a short time) pressing the buttons (113a) of the radiation source magazine and the spacer magazine.

FIG. 20 shows a cross-section through the device (101) according to the invention at the level of the spacer magazine (118). The handle (108) is visible behind the spacer magazine (118). The safety mechanism (123) of the receiving mechanism for device magazines (101) is located at the level of the spacer magazine (118). The safety mechanism (123) encompasses a projection (123a), arranged, for example, in FIG. 20 at the upper right side, which engages in the locking groove (9) of the spacer magazine (118) and captively holds the magazine (118) in the device (101). The safety mechanism (123) further includes a button (123b) in the upper region. By pushing the button (123b), the projection (123a) of the safety mechanism pivots out of the locking groove (9) and releases the magazine (118). In FIG. 20, the safety mechanism (123) is arranged on one side of the spacer magazine (118), the ejection lever mechanism (113) on the other side. The ejection lever mechanism (113) also includes a button (113a) which is operatively connected with the ejector lever (4) of the magazine (118). By pressing the button (113a) of the lever mechanism (113), the ejector lever (4) is rotated upwards and a spacer (119) is released downwards into the working channel (106). FIG. 21 shows the attached working channel (106) of FIG. 20 in an enlarged view. The working channel (106) preferably has a V-shape, so that the chain components are located and guided at the deepest point of the V.

FIG. 22 shows a needle (124) that is inserted into the needle holder (103) of the device (101). The chain components are pushed by the mandrel (107) out the joining and observation unit and into the needle (124).

In the following, the order of operation of the elements of the device (101) for joining chain components will be briefly summarized:

Actuation of the lever mechanism (113) and ejection of a chain component; blocking of the lever mechanism (113) of the actuated magazine;

Displacement of the handle (108) to move the mandrel (107) along the longitudinal axis of the device in the working channel (106) in order to move the ejected chain component into the joining region and observation region (104a, 104b); release of the previously blocked lever mechanism (113);

Repeating steps 1 and 2 until the required chain components have been released;

Pressing and locking the button (119a) of the third lock (119) on the handle (108) to join the chain components by pressing the chain components with the mandrel (107) against the first lock (110);

Release of the first lock (110) by pressing the button (110a);

Displacing the mandrel (107) to move the joined chain components into a needle (124), Spring-loaded or manual return of the handle (108) to its original position; the first lock (110) is closed again only after renewed displacement of the mandrel (107), preferably by engagement of the first extension (113g) in the first opening (110b) of the first lock (110).

In summary, it should be noted that this invention illustrates a fully sterilizable device (101) for the production of radiation source-spacer chains. The device (101) does not require electromechanical parts. The arrangement of the radiation sources and spacers (115, 117) in the chains can be individually and variably configured commensurate with patient-oriented treatment plan.

For the production of radiation source-spacer chains, the described device (101) only requires two magazines (116, 118), which can minimize confusion during assembly of the chain. The magazines (116, 118) are arranged in a row along the longitudinal axis of the device. This creates a clear and user-friendly overview for the operator.

With the encoding of the device (101) and magazine (116, 118) described above, it becomes impossible to swap the radiation source magazine or spacer magazine during insertion into the device (101).

Both magazines (116, 118) transport the stored implants in a working channel (106) which is arranged below the magazines and open on the top. In this channel (105), the implants are pushed to the front of the device (101), where they will later be joined to a so-called strand. This concept prevents the implants from being moved from the rear magazine (118) through the front magazine (116), which could lead to jamming. Furthermore, this concept prevents damage to the mandrel (107) in the event that a magazine (116, 118) is accidentally removed from the entire construction too early. Ejection of the implants into only a single working channel (106) for removal and joining both chain links minimizes the risk of bending the mandrel (107).

Because of this arrangement of magazines (116, 118) with respect to the working channel (106), it is not necessary to move the magazines (116, 118) at an angle relative to the longitudinal axis of the device to change the implants to be ejected.

The magazines preferably contain more than 50 and up to 100 chain components, which are stored in a space-saving carrousel device. However, more than 100 chain components could also be stored in the magazines. Because of the content of the preferred approx. 100 radiation sources or 100 spacers, most radiation source treatments will only be able to be performed with only one of each of the magazines (116, 118).

Due to the interlocks, the magazine (116, 118) can no longer be released when the radiation source stock or the spacer stock is used up.

The magazines (116, 118) are driven with a constant-force spring (3) which always provides the same force. Blocking of this constant-force spring (3) is produced by an externally-driven anchoring system (4).

The magazines (116, 118) can be reused after treatment. They do not contain any electromechanical parts.

The number of radiation sources and spacers (115, 117) remaining in the magazines can be read at any time on the magazines (116, 118). That obviates the need for counting the spent radiation sources and spacers (115, 117) during and after treatment.

The magazines (116, 118) offer optimal radiation protection because the housing (102) is shielded on all sides. The opening (10) of the radiation source magazine (116) is released only after the magazine (116) containing the active radiation sources (115) has been inserted. After removal of the magazine (116) the opening (10) is closed again. Therefore, radiation protection is ensured for the entire duration of application and during transport, i.e. even outside the device. This functional detail can be omitted for magazines having the non-active spacers (117).

Unlike with prefabricated radiation source-spacer chains, the radiation source-spacer chain configuration which is individually tailored for each patient reduces loose radiation source waste. Unused radiation sources (115) and spacers (117) remain in the corresponding magazines (116, 118). Therefore, radiation exposure cannot occur.

In addition, radiation exposure due to released radiation sources in the working channel (106) is prevented by a shield and an indirect view via a minor.

LIST OF REFERENCE SIGNS

1 Magazine
2 Means for receiving chain components or seed repository
3 First tension spring—constant force spring
4 Ejection lever
5 Sliding shutter
6 Recesses
7 Magazine housing
   7a Housing cover
   7b Housing shell
8 Interior bearing ring
9 Locking groove
10 Ejection
11 Encoding bore
12 Opening
13 Upper sprocket
14 Display
15 Marking
16 Inner wall
17 Central opening
18 Spacer
19 Radiation sources
20 First pressure spring—for ejection lever 4
21 Second pressure spring—for sliding shutter 5
22 Release blocking element in case of empty magazines
101 Assembly device for radiation sources
102 Housing
103 Needle holder
104 Joining area and observation unit
   104a Joining area
   104b Observation unit
105 Loading unit
106 Working channel
107 Mandrel
108 External handle
109 Mirror-Lens Unit
   109a Mirror
   109b Lens
110 First lock—Lock in the working channel for assembling chain components
   110a First lock button
   110b Receiving aperture for the first extension of push rod 113g
111 Flap
112 Carriage
113 Lever mechanism
   113a Lever mechanism button
   113b Rod of the lever mechanism button
   113c Lever
   113d First pressure spring piece
   113e Push rod
   113f Second pressure spring piece
   113g First push rod extension
   113h Second push rod extension
114 Magazine
115 Radiation source
116 Radiation source magazine
117 Spacer
118 Spacer magazine
119 Third lock—Lock within the handle
   119a Third lock button
   119b Receiving aperture for the second extension of push rod 113h
120 Installation space for lighting
121 Opening of the loading unit to the working channel
122 Magnetic coupling
123 Magazine safety mechanism
   123a Projection for safety mechanism 123
   123b Button for safety mechanism 123
124 Needle

What is claimed is:

1. A magazine for chain components of a chain with radiation sources, including:
   a housing,
   a means for receiving chain components, which is mounted in a pivoting manner in the housing and has recesses that receive the chain components,
   a tension spring that drives the means for receiving the chain components,
   a sprocket which is firmly coupled with the means for receiving the chain components and is mounted in a pivoting manner in the housing,
   an ejector that ejects the radiation sources, and
   an ejection lever mounted in a pivoting manner in the housing such that, in a first position, the ejection lever engages the sprocket and in a second position, the ejection lever blocks the ejector.

2. The magazine according to claim 1, further comprising a locking slider that opens and closes the ejector, which is mounted in a sliding manner in the housing.

3. The magazine according to claim 2, wherein the ejection lever is biased by a first pressure spring and the locking slider is biased via a second pressure spring.

4. The magazine according to claim 2, wherein the housing comprises:
   locking grooves that engage locking elements mounted on the housing, and/or
   an encoding opening, which acts together with the locking slider in such a way that by insertion of a encoding element into the encoding opening the locking slider releases the ejector.

5. The magazine according to claim 1, wherein the recesses are provided on a circumference of the means for receiving the chain components and
   furthermore a boundary is provided in the housing around the means for receiving the chain components in such a way that a size of a distance between the boundary and the means for receiving the chain components is such that the chain components can be placed and guided in the housing between the means for receiving the chain components and the boundary.

6. The magazine according to claim 1, wherein the tension spring is a constant force spring.

7. The magazine according to claim 6, whereby the housing is provided with a circular inner bearing ring on which the constant force spring as well as the means for receiving the chain components and the sprocket, which is positioned over the means for receiving chain components, are seated.

8. The magazine according to claim 6, wherein the constant force spring is provided below the means for receiving the chain components and the sprocket is provided above the means for receiving the chain components and/or the means for receiving the chain components and the sprocket are formed integrally.

9. The magazine according to claim 8, wherein an area of the means for receiving the chain components, which is in contact with an inner bearing of the housing, is designed to be visible from outside and has at least one mark that indicates a content of the means for receiving chain components.

10. The magazine according to claim 1, wherein the housing consists of radiation-absorbing material.

11. The magazine according to claim 10, wherein the housing consists of stainless steel.

12. The magazine according to claim 1, wherein the ejection lever can be activated from outside through an opening in the housing.

13. The magazine according to claim 1, wherein the ejector is provided such that the chain components are ejected from the magazine and out of the magazine and/or the ejector is provided on a bottom front side of the magazine.

14. The magazine according to claim 13, wherein an element for blocking a further rotation of the means for receiving the chain components after one of the chain components is ejected is implemented in the housing.

15. A system comprising:
   chain components for a chain with radiation sources, and
   a magazine according to claim 1,
   wherein an element for blocking a further rotation of the means for receiving the chain components after one of the chain components has been ejected takes place by joint action of another one of the chain components following the ejected chain component and the ejection lever.

16. The system according to claim 15, wherein the ejection lever in said second position blocks the ejector and said another one of the chain components that is next to the ejector presses against the ejection lever such that a further rotation of the means for receiving the chain components is blocked.

* * * * *